US011274274B2

(12) United States Patent
Tuohey et al.

(10) Patent No.: US 11,274,274 B2
(45) Date of Patent: Mar. 15, 2022

(54) INACTIVATION OF VIRUSES

(71) Applicant: Global Life Sciences Solutions USA LLC, Marlborough, MA (US)

(72) Inventors: Colin R. Tuohey, Marlborough, MA (US); Richard Lee Damren, Marlborough, MA (US); Thomas John Erdenberger, Marlborough, MA (US); Parish M. Galliher, Marlborough, MA (US); Patrick M. Guertin, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 293 days.

(21) Appl. No.: 15/561,826

(22) PCT Filed: Apr. 12, 2016

(86) PCT No.: PCT/EP2016/057971
§ 371 (c)(1),
(2) Date: Sep. 26, 2017

(87) PCT Pub. No.: WO2016/169803
PCT Pub. Date: Oct. 27, 2016

(65) Prior Publication Data
US 2018/0119084 A1  May 3, 2018

Related U.S. Application Data

(60) Provisional application No. 62/149,813, filed on Apr. 20, 2015.

(51) Int. Cl.
*C12M 1/12* (2006.01)
*C12M 1/00* (2006.01)
(Continued)

(52) U.S. Cl.
CPC .......... *C12M 37/00* (2013.01); *A61L 2/0023* (2013.01); *A61L 2/0035* (2013.01); *A61L 2/081* (2013.01);
(Continued)

(58) Field of Classification Search
CPC ........ C12M 23/14; C12M 23/28; H05B 6/108
See application file for complete search history.

(56) References Cited

U.S. PATENT DOCUMENTS 5,965,086 A   10/1999  Rose et al.
7,420,183 B2   9/2008  Kaiser et al.
(Continued)

FOREIGN PATENT DOCUMENTS

| CA | 2 096 888 C | | 4/2004 |
|---|---|---|---|
| CN | 2540980 Y | * | 3/2003 |
| CN | 1569031 A | | 1/2005 |

OTHER PUBLICATIONS

PCT International Search Report and Written Opinion for PCT Application No. PCT/EP2016/057971 dated Jun. 10, 2016 (9 pages).
(Continued)

*Primary Examiner* — William H. Beisner
(74) *Attorney, Agent, or Firm* — Eversheds Sutherland (US) LLP (57) ABSTRACT

The invention discloses a bioreactor apparatus (1;101;201;301) for cultivation of cells comprising: a) a disposable bioreactor vessel (2) with one or more walls (3,4,5) defining an inner volume (6), at least one port (10) in a wall, wherein the disposable bioreactor vessel is positioned in a rigid support structure (8;108); and b) a heater (9;109;209;309), capable of heating an amount of culture medium to a target temperature in the range of 55-95° C., while the amount of culture medium is being confined in or conveyed to the inner volume.

11 Claims, 10 Drawing Sheets

(51) Int. Cl.
  *C12M 1/02* (2006.01)
  *C12M 1/34* (2006.01)
  *A61L 2/00* (2006.01)
  *A61L 2/08* (2006.01)
  *C12N 7/00* (2006.01)
  *C12M 1/06* (2006.01)

(52) U.S. Cl.
  CPC ............ *C12M 23/14* (2013.01); *C12M 23/26* (2013.01); *C12M 23/28* (2013.01); *C12M 41/16* (2013.01); *C12M 41/22* (2013.01); *C12N 7/00* (2013.01); *A61L 2/0017* (2013.01); *A61L 2202/14* (2013.01); *A61L 2202/23* (2013.01); *C12M 23/06* (2013.01); *C12M 27/02* (2013.01); *C12M 29/00* (2013.01); *C12N 2795/00061* (2013.01)

(56) References Cited

U.S. PATENT DOCUMENTS

| | | | |
|---|---|---|---|
| 7,629,167 B2 | 12/2009 | Hodge et al. | |
| 2004/0062140 A1 | 4/2004 | Cadogan et al. | |
| 2006/0065276 A1 | 3/2006 | Kammer et al. | |
| 2010/0075405 A1* | 3/2010 | Broadley | C12M 23/14 435/286.1 |
| 2010/0317102 A1* | 12/2010 | Suzuki | C12M 41/14 435/366 |
| 2012/0214204 A1 | 8/2012 | Hart et al. | |
| 2013/0197437 A1* | 8/2013 | Faries | A61M 5/44 604/113 |
| 2014/0293734 A1 | 10/2014 | Kauling et al. | |
| 2015/0218501 A1 | 8/2015 | Kauling et al. | |

OTHER PUBLICATIONS

Japanese Office Action for JP Application No. 2017-554814 dated Nov. 18, 2019 (7 pages).
Non-Final Office Action for U.S. Appl. No. 15/718,831 dated Jan. 23, 2020 (14 pages).
Bragt et al., "Effects of Sterilization on Components in Nutrient Media," Papers presented at symposium organized by the Department of Horticulture, Agricultural University, Wageningen, The Netherlands, on Mar. 4, 1970, published as Miscellaneous Papers 9 (1971), 151 pages.
Pohlscheidt et al., "Implementing High-Temperature Short-Time Media Treatment in Commercial-Scale Cell Culture Manufacturing Processes," Appl. Microbiol Biotechnol, 2014, 98:2965-2971.
European Office Action for EP Application No. 16715560.5 dated Sep. 24, 2020 (4 pages).
U.S. Non-Final Office Action for U.S. Appl. No. 15/718,831 dated Nov. 25, 2020 (20 pages).
Wolff et al., "Downstream Processing of Cell Culture-Derived Virus Particles", Expert Review Vaccines, 2011, 10(10):11451-1475.
Chinese Office Action for CN Application No. 2016800227826 dated Sep. 7, 2020 (26 pages with English translation).

* cited by examiner

INACTIVATION OF VIRUSES

CROSS REFERENCE TO RELATED APPLICATIONS

This application claims the priority benefit of PCT/EP2016/057971 filed on Apr. 12, 2016 which claims priority benefit of U.S. Provisional Application No. 62/149,813 filed Apr. 20, 2015. The entire contents of which are hereby incorporated by reference herein.

TECHNICAL FIELD OF THE INVENTION

The present invention relates to manufacturing of biopharmaceuticals, and more particularly to inactivation of viruses before and after cultivation of cells. The invention also relates to a bioreactor apparatus and to an induction heater for virus inactivation.

BACKGROUND OF THE INVENTION

The bioprocessing industry has traditionally used stainless steel tanks in bioreactors for cell cultivation expression of therapeutic proteins etc. These tanks are designed to be reused after cleaning and/or sterilization. Cleaning and sterilization are however costly labor-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last fifteen years—that of using plastic, single-use disposable bags to replace the usual stainless steel tanks. In large-scale operations, the preferred solution is to use flexible bags supported by an outer stainless steel support vessel. This allows single-use operation in scales up to several cubic meters.

When bacterial cells are cultivated in stainless steel bioreactors, it is common practice to inject steam in the bioreactor to sterilize the culture medium. This inactivates both microorganisms and viruses such as bacteriophages. As plastic bags are sensitive to high temperatures, the culture medium is normally sterile filtered instead, before being added to a disposable bioreactor. Sterile filtration removes microorganisms but not viruses like bacteriophages.

Accordingly there is a need for a methodology and equipment that enables inactivation of viruses such as bacteriophages before cultivation in disposable bioreactors.

SUMMARY OF THE INVENTION

One aspect of the invention is to provide a bioreactor apparatus for cultivation of cells under virus-free conditions. This is achieved with an apparatus as defined in claim 1.

A technical advantage is that the apparatus is able to solve the problem of bacteriophage contamination using single use technology. Commercially, the single use bioreactor platform is expanding into the microbial space and there is an inherent lack of a way to deal with potential phage contamination in a streamlined manner with single use technology. The ability to heat the bag or tubing material along with the media to elevated temperatures, while still mixing and then cooling down for further processing all in a single system is a simplified approach. Alternatively, the method of using inductive heating (or other heating methods described) to heat the media prior to introduction into the bioreactor can potentially reduce the hold time required by having even higher temperatures. Other applications within bioprocessing that need fluid heat exchange can potentially be adapted to a single use platform with the integration of this technology.

Cell culture media and specifically media intended for microbial fermentation needs to be treated in order to reduce the likelihood for bacteriophage contamination. Holding the medium at a temperature of 60° C. for a duration of 10-12 hours will reduce the presence of contaminating organisms such as bacteriophages that can inhibit the growth of microbial fermentations and produce other complicating factors. Increased temperatures, such as 90° C. for example, can limit the time required to achieve the same result in performance. Bacteriophages are ubiquitous in organic matter and therefore it is beneficial to perform a heat treatment step during microbial cell culture to reduce quantities of active contaminants after or during sterilization of the medium into the bioreactor vessel. The nature of single-use technology for biopharmaceutical processing presents an inherent challenge and difficulty to adapting these processes to the platform, since many of the materials used cannot withstand elevated temperatures under stress. Traditional methods of sterilizing the media in the bioreactor via saturated steam are not possible using single use technology and therefore a system that is capable of being pre-sterilized followed by heat treatment is needed.

A second aspect of the invention is to provide a method for virus inactivation of culture media. This is achieved with a method as defined in the claims.

A third aspect of the invention is to provide a method for cell cultivation in culture media where viruses have been inactivated. This is achieved with a method as defined in the claims.

A fourth aspect of the invention is to provide a method for virus inactivation in downstream settings. This is achieved with a method as defined in the claims.

A fifth aspect of the invention is to provide an induction heater suitable for virus inactivation. This is achieved with a heater as defined in the claims.

Further suitable embodiments of the invention are described in the dependent claims.

DRAWINGS

FIG. 7 a) shows a heater according to the invention, cross section.

FIG. 7 b) shows a heater according to the invention, side view.

DEFINITIONS

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

Any directional terms such as "top", "bottom", "above", "below" "up", "down" and "height" herein refer to the devices as they appear in the drawings. Joinder references (e.g., joined, attached, coupled, connected, and the like) are to be construed broadly and may include intermediate members between a connection of elements and relative movement between elements. As such, joinder references do not necessarily imply that two elements are connected directly and in fixed relation to each other. Further, various elements discussed with reference to the various embodiments may be interchanged to create entirely new embodiments coming within the scope of the present invention.

DETAILED DESCRIPTION OF EMBODIMENTS

This invention describes a system that is capable of containing a single use bioreactor bag and heating the components contained within to an elevated temperature and controlling that temperature with agitation for an extended duration to achieve the desired performance result. The system may contain a vessel that is jacketed, allowing the flow of heat transfer fluid in and out of the jacket with a separate temperature control unit (TCU) for the purpose of controlling the temperature inside the bioreactor vessel. The controlling mechanism may be performed through a feedback loop comprised of a temperature sensor inserted non-invasively into a single use bioreactor bag and connected to a software platform capable of proportional-integral-derivative (PID) control in communication with the TCU.

Cell culture media can be sterile filtered into a bioreactor bag and then agitated via an impeller. The desired temperature set point can input to a control unit and the TCU can heat up the fluid and circulate it through the jacket until the media temperature is reached. The system can then control the temperature of the fluid while agitating for the duration required. Once heat treatment is performed, the system is capable of cooling and controlling the media within the bioreactor bag to the desired process temperature. This can also be done in a jacketed mixer.

Alternatively, a system is described for heat treating the medium in a continuous method during or immediately post sterile filtration when introduced into the single use bioreactor. This is achieved by passing the fluid through a separate bag or tubing structure that is in communication with the bioreactor bag via tubing or conduit bag structure. The separate bag or tubing structure is capable of heat transfer and may be contained between one or more heat transferring plates or tubes that heat the internal medium to the desired temperature to achieve heat treatment as it enters the single use bioreactor bag. The bioreactor bag contained within said vessel is then capable of maintaining the medium at the desired temperature for the prescribed duration (if additional time necessary) in order to achieve the heat treatment effective for further processing. The heat transfer can be performed via a Peltier heater, inductive heating coil or through a fluid exchange TCU capable of achieving and controlling the desired process output temperature. The system is then capable of cooling the bioreactor contents to the desired process temperature.

A separate bag or tubing can be used as a heat exchanger and connected to a media reservoir on one end and to a bioreactor bag on the other end. The media can be passed from the reservoir through the heat exchanger bag and the internal fluid heated such that the desired temperature is achieved for the required duration upon exiting the heat exchanger bag. The media can then flow into the bioreactor bag and either be maintained at the heat treatment temperature or the temperature may be reduced to the desired process temperature. The method of heating can be a bag that is pressed between two plates or encased in a tubular conduit where the plates or conduit are heated either thermoelectrically with a Peltier type unit or with circulating heat transfer fluid connected to a TCU.

This secondary vessel can also be a jacketed mixer containing a single use mixer bag that has the same heat transfer function and capability of the bioreactor vessel with mixing capability in communication with the bioreactor vessel.

In one aspect, illustrated by FIGS. 1-7, the present invention discloses a bioreactor apparatus 1;101;201;301 for cultivation of cells. The apparatus comprises a) a disposable bioreactor vessel 2 and b) a heater 9;109;209;309, as described in further detail hereinunder.

a) The disposable bioreactor vessel 2 has one or more walls 3,4,5, which together define an inner volume 6. It may be a bag, in which case the walls can suitably be made from flexible plastic sheet material, such as polyethylene or a laminate comprising polyethylene, e.g. joined by welding. The vessel may be generally cylindrical, in which case it may have an upstanding side wall 3, a bottom wall 4 and a top wall 5. It may however also have other shapes, such as generally cuboid, with four upstanding side walls, a bottom wall and a top wall. In one or more of the walls, the vessel has at least one port 10, suitably at least two ports, to allow introduction and removal of materials to the inner volume. The vessel may e.g. have a culture medium port—located e.g. in the top wall, a drain port—located e.g. in or adjacent to the bottom wall, a gas inlet port and a gas exhaust port—located e.g. in the top wall and further sampling and sensor ports. The inner volume 6 may be at least 4 L, such as at least 10 L, at least 25 L, at least 50 L, at least 100 L, at least 400 L, 4-2500 L, 10-2500 L, 25-2500 L, 25-500 L, 50-2500 L, 100-2500 L or 400-2500 L. Further, the vessel may comprise at least one agitator, such as at least one magnetically driven impeller, in the inner volume. It may e.g. comprise one or more magnetic impellers mounted on a shaft which can be rotatably mounted to e.g. the bottom wall and arranged to be driven by an external magnetic motor drive unit, e.g. as described in WO2005118771A1, which is hereby incorporated by reference in its entirety. The vessel is positioned in a rigid support structure 8;108, which may have one or more walls 11;111,12;112,13;113 defining an inner support volume 14;114 and the vessel can suitably have a shape conforming to, or essentially conforming to, the shape of the inner support volume. The vessel can fill out most of, or essentially all of the inner support volume. When filled with a liquid, the vessel may fit tightly inside the inner support volume, with intimate contact between the vessel walls and the support structure walls.

b) The heater 9;109;209;309 is capable of heating an amount of culture medium to a target temperature in the range of 55-95° C., while this amount of culture medium is being confined in or conveyed to the inner volume of the disposable bioreactor vessel. The amount of culture medium may be all, or substantially all of the culture medium to be used in a subsequent cultivation of cells, and it may e.g. correspond to at least 20%, at least 50% or at least 60% of the inner volume of the disposable bioreactor vessel. In absolute terms, the amount can e.g. be at least 1 L, at least 10 L, at least 25 L, at least 50 L, at least 100 L, at least 400 L, 4-2500 L, 10-2500 L, 25-2500 L, 25-500 L, 50-2500 L, 100-2500 L or 400-2500 L. The heater can be thermostated and it can be capable of maintaining the amount of culture medium within an interval of the target temperature+/−5° C. It may even be capable of maintaining the temperature at the target temperature+/−2° C., +/−1° C. or +/−0.5° C.

Figure 1:
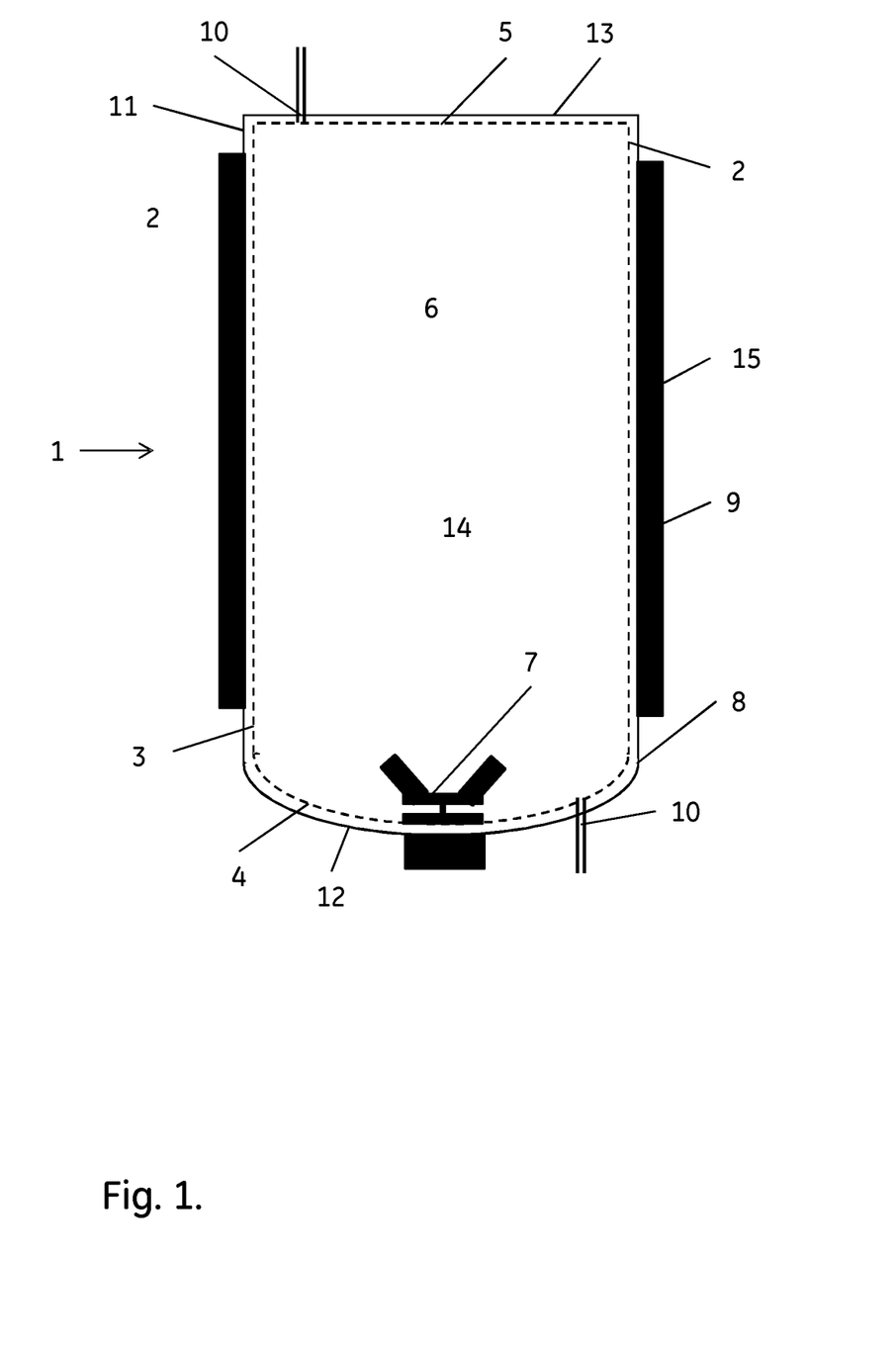
FIG. 1 shows a bioreactor apparatus according to the invention, side view.
Figure 2:
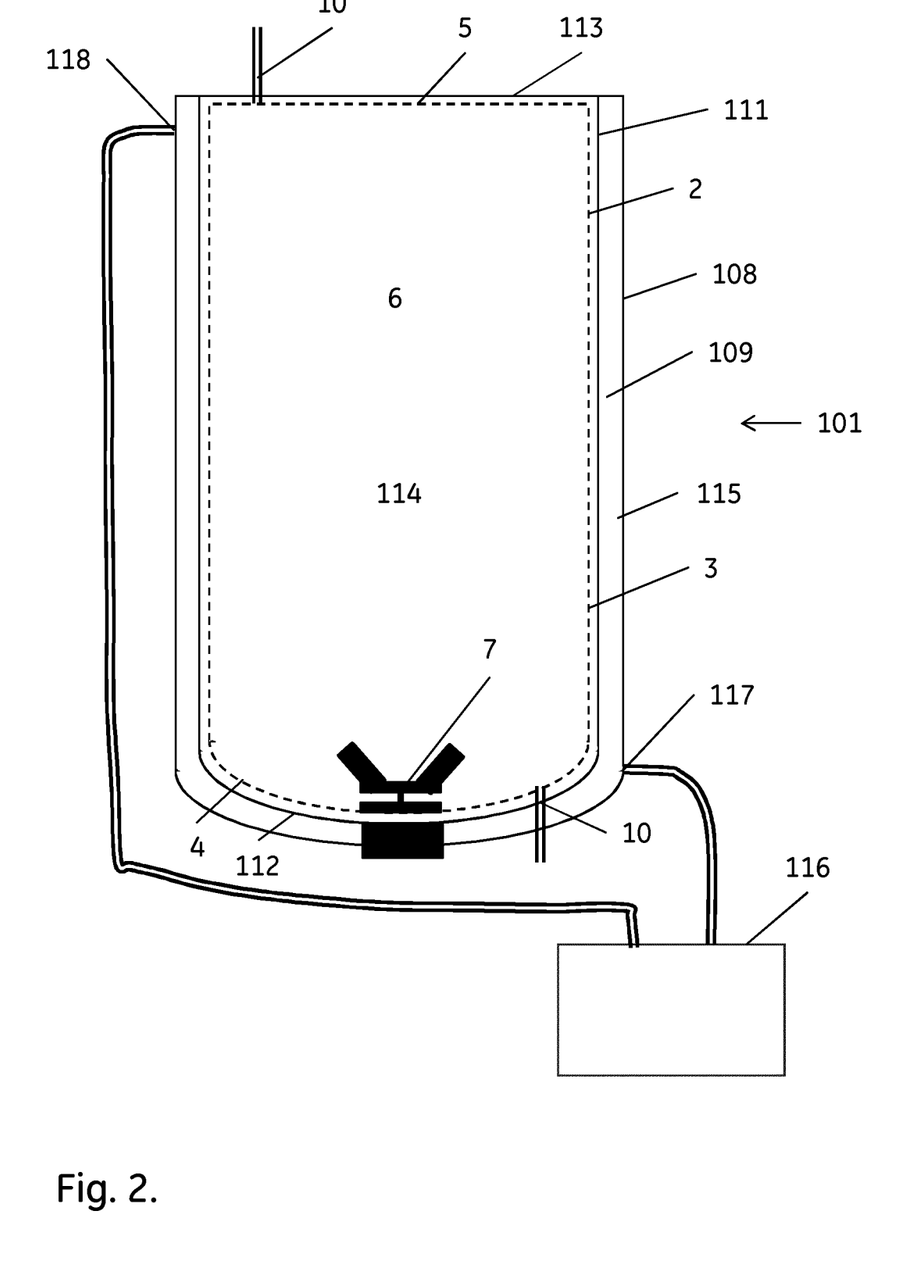
FIG. 2 shows a bioreactor apparatus according to the invention, side view.
Figure 5:
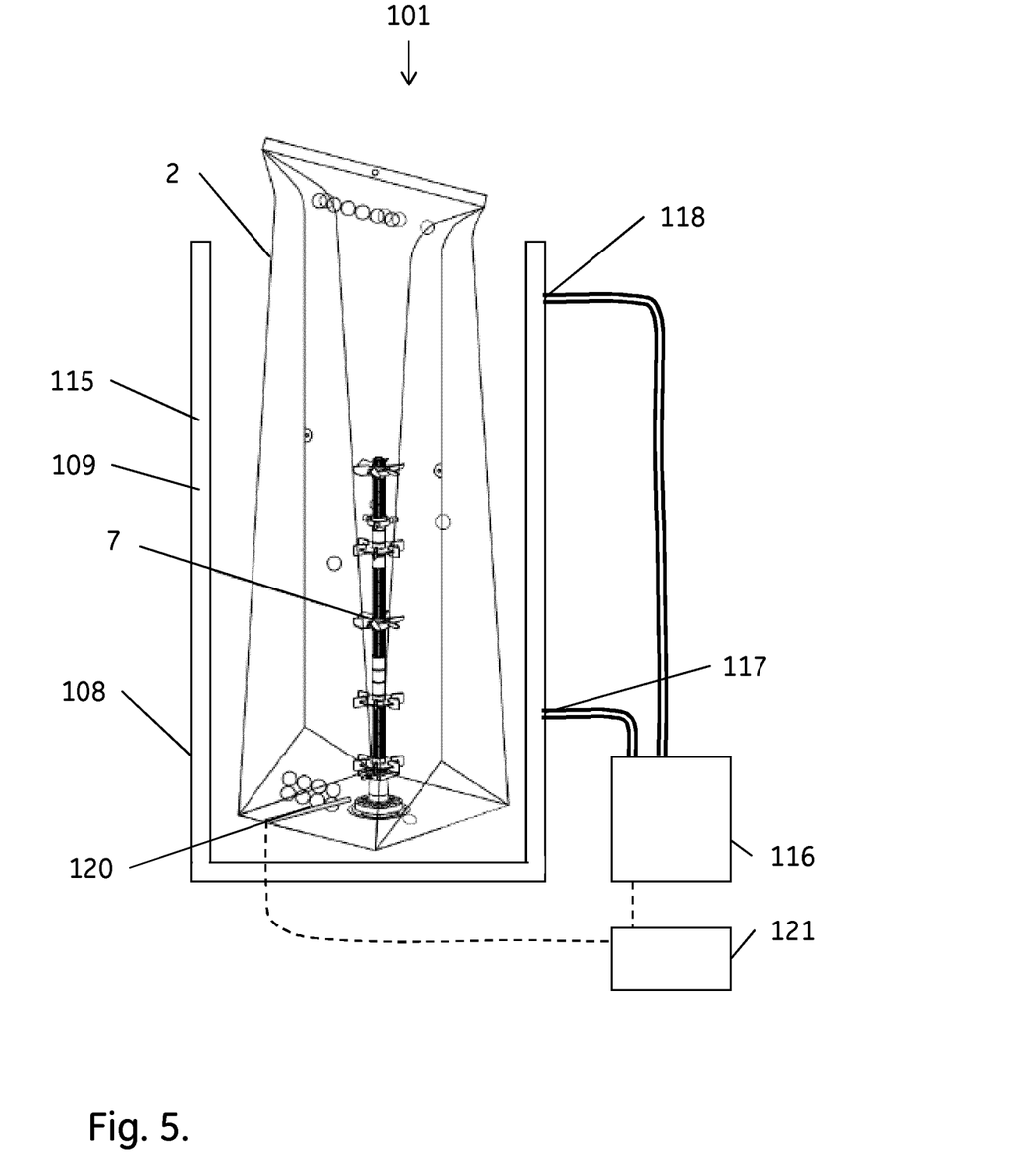
FIG. 5 shows a bioreactor apparatus according to the invention, side view.

In some embodiments, illustrated by FIGS. 1, 2 and 5, the support structure 8;108 comprises at least part of the heater 9;109. These embodiments are particularly suitable for heating the culture medium when it is confined in the inner volume of the disposable bioreactor vessel. The heater 9 can e.g. comprise a heating mantle 15, which can be in intimate contact with said disposable bioreactor vessel 2. The heating mantle can be integral with the rigid support structure 8, e.g. mounted on the inside of one or more of the support structure walls. Examples of heating mantles include electrical heating mantles well known in the art.

The heater can also comprise a jacket 115 in contact with the disposable bioreactor vessel 2 and a supply 116 of temperature-control liquid. This supply (alternatively called a temperature control unit—TCU) can be fluidically connected to a temperature-control liquid inlet 117 and suitably also to a temperature-control outlet 118 in the jacket 115, such that the liquid is circulated through the jacket. Typically, the jacket can be integrated with the support vessel and may comprise double walls in the vessel where the liquid can circulate between the walls. The temperature control liquid can e.g. be water, an aqueous liquid (e.g. a solution of a substance in water) or an oil.

Figure 3:
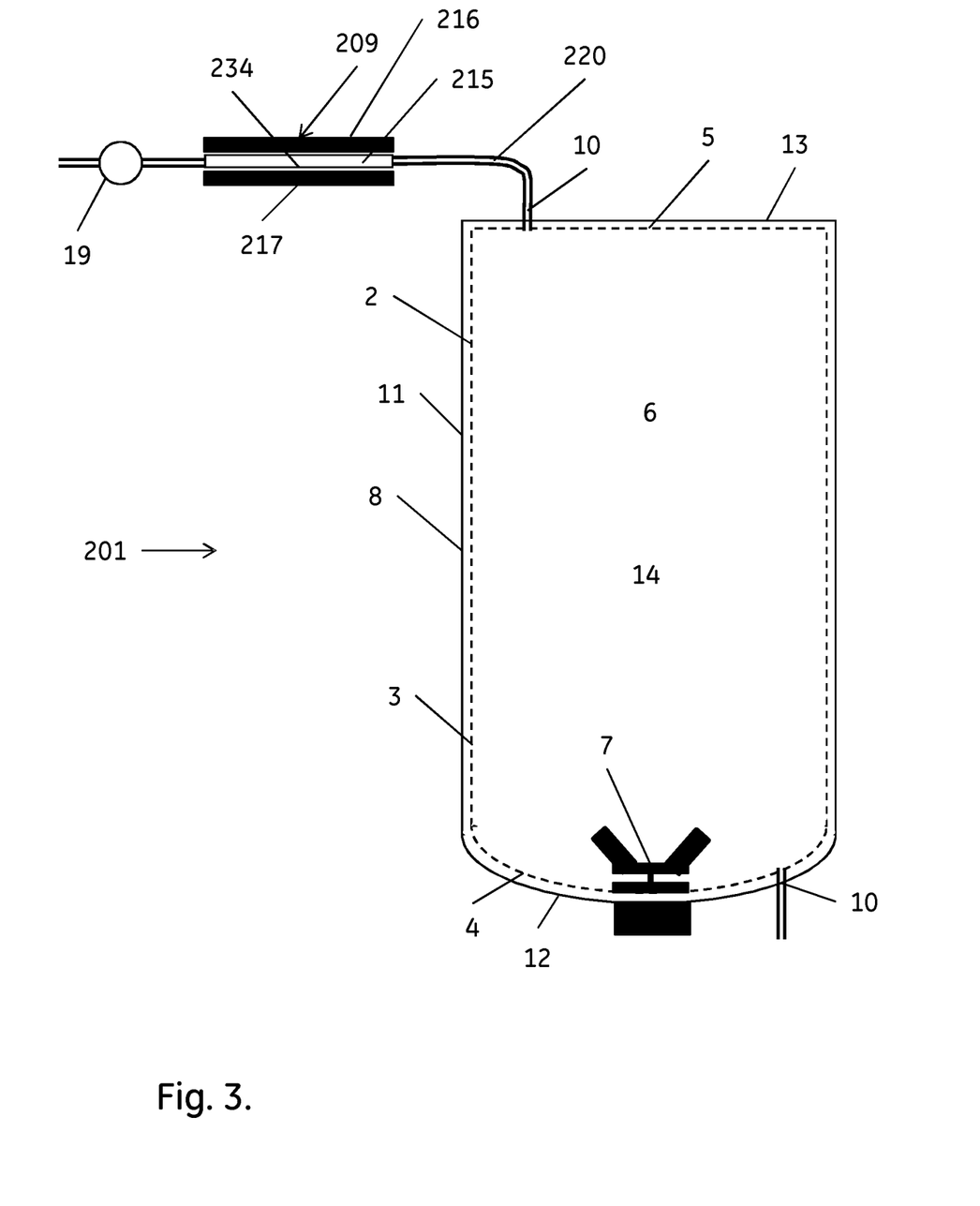
FIG. 3 shows a bioreactor apparatus according to the invention, side view.
Figure 6:
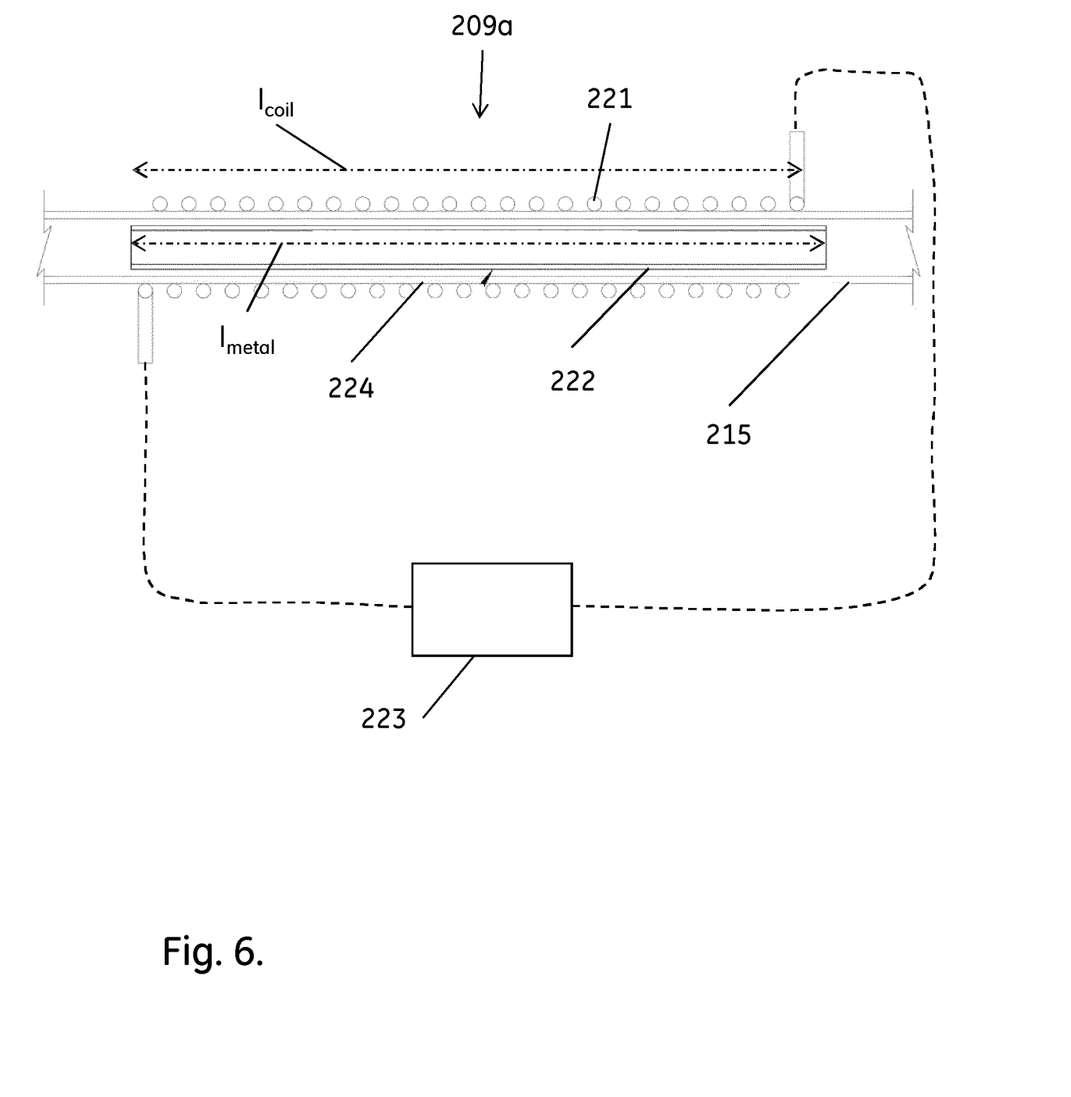
FIG. 6 shows a heater according to the invention, side view
Figure 7:
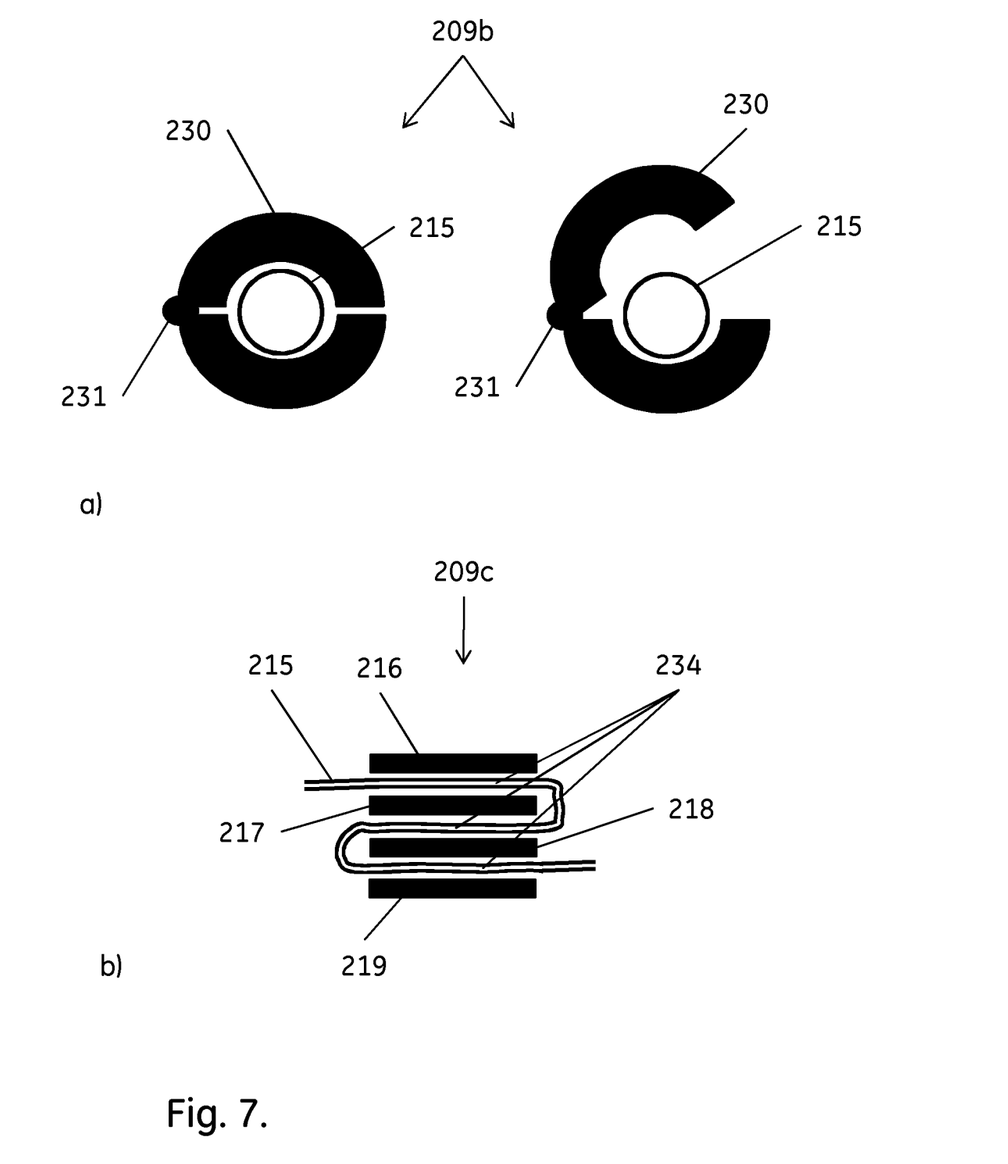

In certain embodiments, illustrated by FIGS. 3 and 6-7, the heater 209;209a;209b;209c comprises a disposable heater conduit 215, which is fluidically, such as aseptically, connected to a port 10 in a wall of the disposable bioreactor vessel; and at least one heating element 216,217;221 positioned to heat the disposable heater conduit. The disposable heater conduit can suitably also be fluidically (aseptically) connected to a reservoir of culture medium (not shown), such that culture medium can be conveyed from the reservoir through the disposable heater conduit to be heated and then further conveyed to the inner volume of the disposable bioreactor vessel. The bioreactor apparatus 201 may comprise a pump 19, such as a peristaltic pump or a pump with a disposable pump head, arranged to convey culture medium through the disposable heater conduit 215 into the disposable bioreactor vessel. Alternatively, or additionally, the disposable bioreactor vessel may be positioned to allow gravity flow of culture medium from a reservoir via the disposable heater conduit into the disposable bioreactor vessel, e.g. by placing the bioreactor vessel in a lower position than the disposable heater conduit and the reservoir. The disposable heater conduit 215 can e.g. be a flexible bag or a flexible tubular structure in contact with or adjacent to one or more heating elements 216,217. The heating element(s) can e.g. be electrical heating elements, Peltier elements or a jacket with circulating temperature control liquid, in which case the heating element(s) is/are suitably placed in contact with the disposable heater conduit. Alternatively, the heating element(s) can e.g. be IR irradiators or a microwave heater, which can be placed adjacent to the disposable heater conduit in a position where the conduit is exposed to the IR or MW radiation. Also, the heating element(s) can be one or more induction coils 221 at least partially surrounding one or more segments 224 of the disposable heater conduit 215, as further discussed below. In this case one or more metallic structures 222 are suitably placed inside the conduit segment(s) to provide an induction heater in combination with the coil(s). The metallic structures can be placed in direct contact with culture medium passing through the conduit and may e.g. be one or more lengths of metal pipe, metal mesh (e.g. tubular mesh), metal braid or metal coil. Other possible geometries might a bundle of metal rods, a bundle of hollow metal tubes, a spiral coil, objects with lobe shaped cross sections, etc. The length of this assembly would be selected so as to produce sufficient heating of the liquid while it is resident in the conduit segment as the liquid flows through the system. The material can suitably be stainless steel or another metal which does not contaminate the culture medium with corrosion products. For more details about the induction heater 209a, see below.

The disposable heater conduit 215 can be a flexible bag or a flexible tubular structure confined in one or more segments 234 of generally flat shape between one or more generally flat heating elements 216,217,218 and optionally one or more inert counterplates 219 (support plates without heating function). If more than one segment of the conduit is confined, the segments can e.g. be arranged in line or the conduit can be folded over to form a stack of confined segments, as in FIG. 7 *b*). Alternatively, one or more segments of the disposable heater conduit is/are confined within one or more generally duct-shaped heating elements 230. The disposable heater conduit 215 may e.g. be tubular and confined in a tubular heating element 230, which may have a hinge 231 and may open as a clamshell and allow easy replacement of the conduit. The cross sections of the tubular conduit and the tubular heating elements may e.g. be circular, oval or rectangular, or any other suitable shape.

Figure 4:
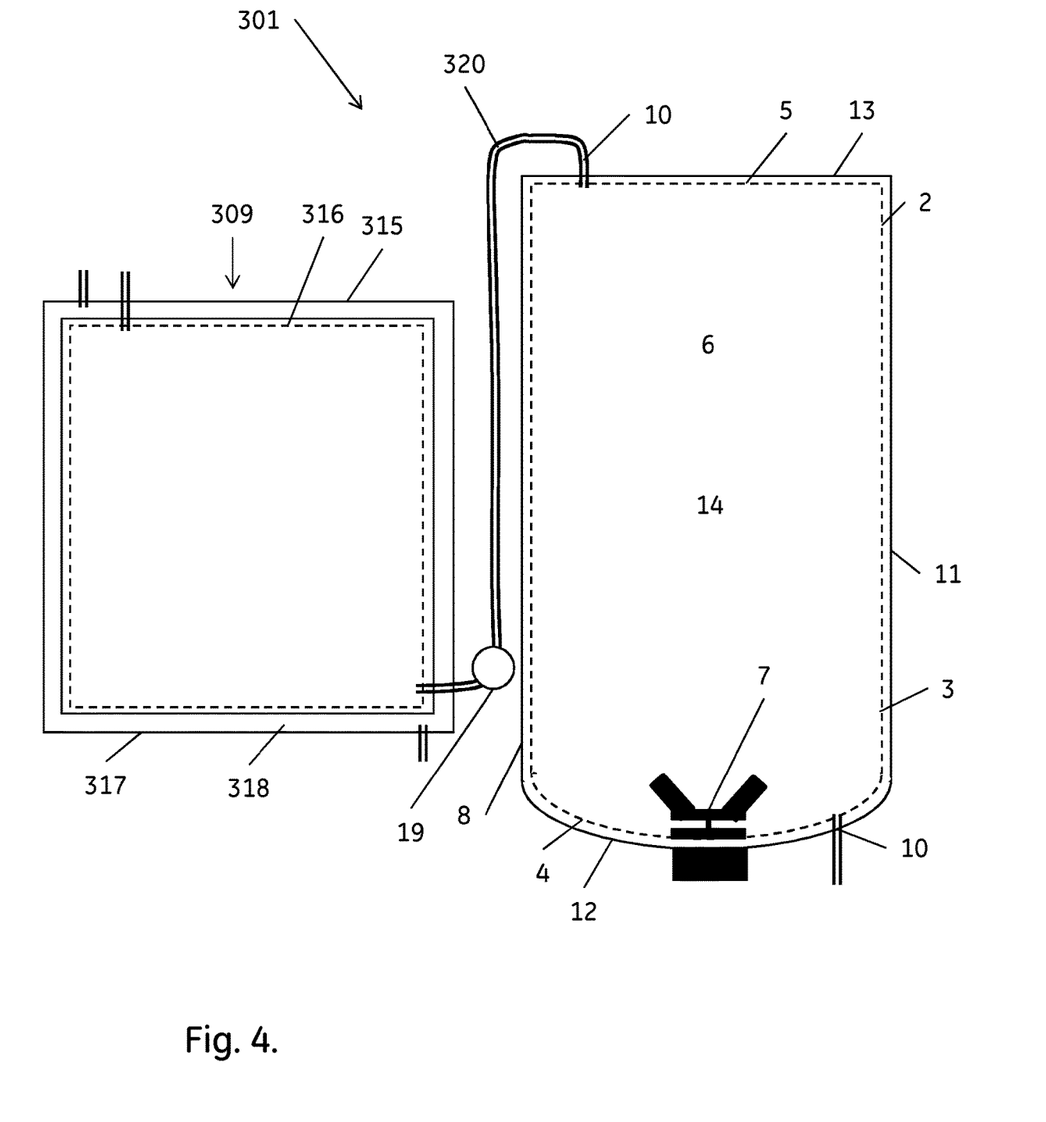
FIG. 4 shows a bioreactor apparatus according to the invention, side view.

In some embodiments, illustrated by FIG. 4, the heater 309 comprises an external disposable heating vessel 315, which is fluidically, such as aseptically, connected to a port 10 in a wall of the disposable bioreactor vessel. This allows separate heating of the culture medium in the heating vessel and subsequent conveying of the medium to the inner volume of the disposable bioreactor vessel. The external disposable heating vessel 315 can e.g. comprise a flexible heating bag 316 positioned in a rigid heating vessel support structure 317 with an integral heating mantle or a jacket 318 in contact with the flexible heating bag. The heating vessel may optionally comprise agitation means such as an internal agitator (e.g. a magnetically driven impeller rotatably mounted inside a flexible heating bag) or an external circulation loop. The bioreactor apparatus 301 may further comprise a pump 19, such as a peristaltic pump or a pump with a disposable pumphead, arranged to convey culture medium from the external disposable heating vessel 315 into the disposable bioreactor vessel. Alternatively, or additionally, the disposable bioreactor vessel may be positioned to allow gravity flow of culture medium from the external disposable heating vessel into the disposable bioreactor vessel, e.g. by placing the bioreactor vessel in a lower position than the external disposable heating vessel.

In certain embodiments, the disposable bioreactor vessel 2 is presterilized, such as by gamma irradiation sterilization. It can be supplied with aseptic connectors well known in the art and/or closed lengths of tubing attached to the ports, allowing aseptic connection to further units or tubing, either by connection via the aseptic connectors or by aseptic welding of tubing according to well-known methods. Also any disposable heater conduit and/or any external disposable heating vessel can be supplied presterilized with aseptic connectors and/or closed lengths of tubing to allow aseptic connection with the disposable bioreactor vessel and the culture medium reservoir.

In some embodiments, the disposable bioreactor vessel 2 and optionally any disposable heater conduit 215 and/or any external disposable heating vessel 315 comprise(s) one or more temperature sensors 120. This allows for verification and feedback loop control of the temperature and/or the temperature profiles. The temperature sensors 120 may e.g. be electrically or electromagnetically connected to a control unit 121, which is also electrically or electromagnetically connected to the heater 9;109;209;309, e.g. a supply (TCU) 116 of temperature control liquid, to enable feedback loop control of the temperature.

In a second aspect, the invention discloses a method of inactivating viruses in a culture medium. This method comprises the steps of a) providing a culture medium; b) heating the culture medium to a temperature of 55-95° C. and maintaining this temperature; and c) cooling the culture medium, as described in further detail hereinunder. The viruses can be bacteriophages, but they can also be pathogenic or non-pathogenic animal or human viruses. The method can suitably be carried out under aseptic conditions. It can suitably be conducted in the bioreactor apparatus 1;101;201;301 described in any of the above embodiments and step b) can then comprise heating the culture medium with heater 9;109;209;309.

a) The culture medium can be a culture medium suitable for cultivation of e.g. microorganisms or animal cells. A large number of such media are available from companies like GE Healthcare Life Sciences (ActiCHO™, HyClone™ etc.) and Life Technologies (LB Broth™, Gibco™ etc.). The culture medium can suitably be sterile filtered, i.e. filtered through a sterilization grade filter. Some media components like vitamins and antibiotics can be temperature-sensitive and if this is an issue, the method can be applied on a culture medium without these components and they can be added to the medium after cooling. It can then be advantageous to filter the components through a virus-retentive filter before being added to the culture medium, in order to remove any viruses present in the components. Virus-retentive filters as used in e.g. monoclonal antibody processing can be used for this purpose, but it is also possible to use ultrafiltration membranes, through which small molecules like vitamins and antibiotics will pass, but not virus particles.

b) The culture medium is heated to a temperature of 55-95° C. and maintained at this temperature. It may e.g. be maintained for 10 s to 24 h, such as 30 s to 24 h, 30 s to 12 h, 30 s to 6 h, 30 s to 1 h, 30 s to 10 min or 10 s to 5 min. Depending on the temperature, these times are sufficient for deactivation of viruses like bacteriophages. 10-12 h may be required at 60° C., while at 90° C. dramatically shorter times are required. The temperature can be maintained within an interval of a target temperature+/−5° C., such as the target temperature+/−2° C., +/−1° C. or +/−0.5° C., wherein the target temperature is within 55-95° C. A precise control of the temperature prevents the risk of overheating and damaging any potentially sensitive components, while ensuring that the temperature needed for deactivation is reached. For this reason it can also be advantageous if no part of the culture medium is exposed to a temperature more than 10, 20 or 30° C. above the target temperature. To avoid damage to potentially sensitive plastics and other construction materials it can also be an advantage if no part of any disposable bioreactor vessel, disposable heater conduit and/or external disposable heating vessel is exposed to a temperature more than 10, 20, 30, 40 or 50° C. above the target temperature.

c) After the heating step b), the culture medium is cooled. It can advantageously be cooled down to a temperature suitable for cell cultivation, e.g. about 37° C. for many animal cells or 30-40° C. for many bacteria. The cooling may be performed passively, by heat exchange with the ambient environment, or actively by application of a cooling system.

In some embodiments, step b) is carried out directly in the disposable bioreactor vessel or after step b) or c), the culture medium is conveyed to the disposable bioreactor vessel. This allows for cultivation of cells in the heat treated culture medium. Accordingly, in certain embodiments, the method comprises, after step c), a step d) of cultivating cells in the culture medium. These cells may be microorganisms, such as bacteria, e.g. comprising a species selected from the group of genera consisting of *Escherichia, Bacillus, Lactobacillus* and *Pseudomonas*. Alternatively, the cells can be animal cells, such as mammalian or insect cells, e.g. comprising cells selected from the group consisting of CHO cells, NS0 murine myeloma cells, MDCK cells, Vero cells, PER.C6 cells, Sf9 cells and Sf21 cells.

In a third aspect, the invention discloses a method of cultivating cells in culture media which have been subjected to the virus inactivation methods described in steps a) and b) above. The cultivation is then carried out according to step c) as discussed above.

In a fourth aspect the invention discloses a method for virus inactivation of a liquid sample. This method comprises the steps of:

a) Providing a liquid sample comprising a target biomolecule. The liquid can suitably be a liquid obtained in any step of a bioprocess upstream or downstream operation. It can e.g. be a cell broth, a clarified cell broth, a filtrate or an eluate or flowthrough fraction from a previous chromatography step. The target biomolecule can e.g. be a protein (e.g. an antibody or a recombinant protein), a polysaccharide or a nucleic acid (e.g. a plasmid). The target biomolecule can e.g. be a biopharmaceutical. The liquid may be suspected of containing viruses or it may have been shown to contain viruses. The method may also be applied as a precautionary method, in case the liquid should contain viruses.

It is also possible to adjust the composition of the liquid before application of step c). The pH can e.g. be lowered and virus inactivating agents such as detergents and/or organic solvents may be added.

b) Providing a heater 9;109;209;309. This can be any of the heaters described above.

c) Heating the sample to a temperature of 55-95° C. and maintaining this temperature. The temperature can e.g. be maintained for 10 s to 24 h, such as 30 s to 24 h, 30 s to 12 h, 30 s to 6 h, 30 s to 1 h, 30 s to 10 min or 10 s to 5 min.

The temperature can e.g. be maintained within an interval of a target temperature+/−5° C., such as the target temperature+/−2° C., +/−1° C. or +/−0.5° C., wherein the target temperature is within 55-95° C.

d) Cooling the sample. It can advantageously be cooled down to ambient temperature, e.g. 15-35° C. or 15-25° C. The cooling may be performed passively, by heat exchange with the ambient environment, or actively by application of a cooling system.

Figure 10:
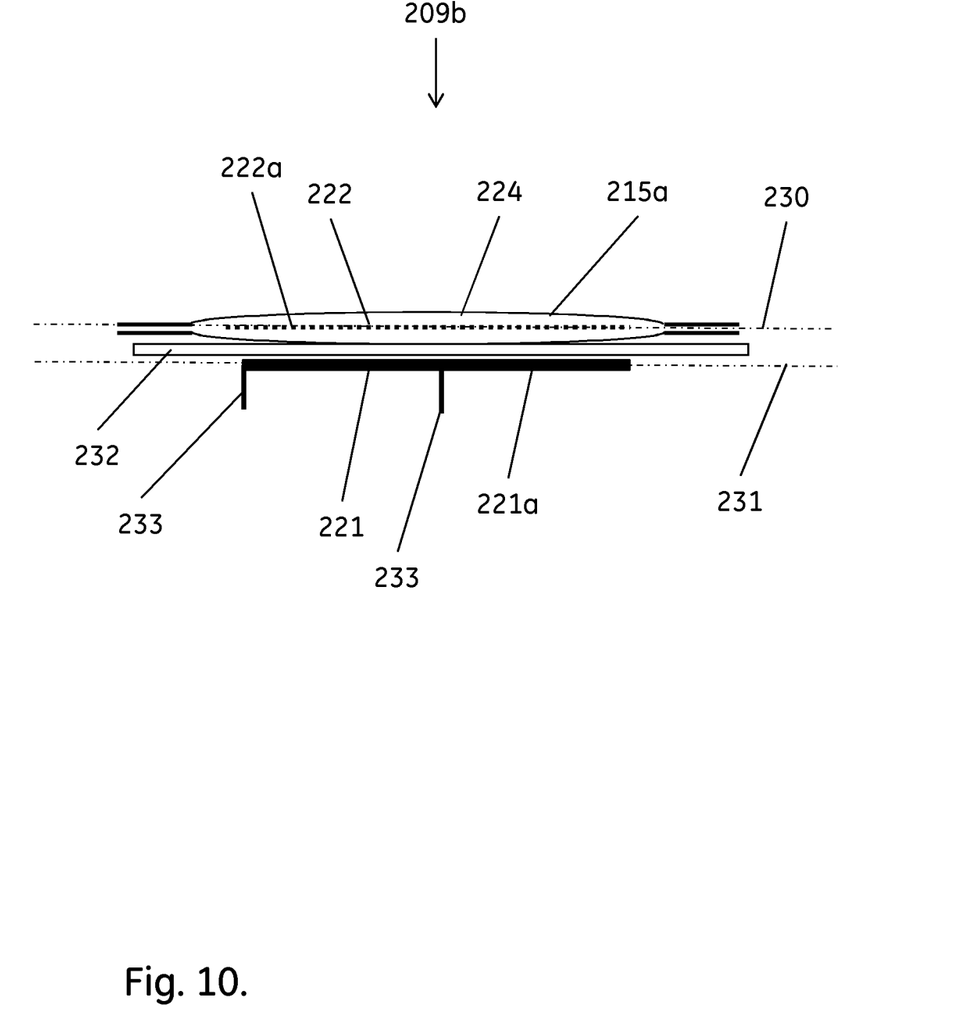
FIG. 10 shows a bioreactor according to the present invention, planar view.

In a fifth aspect, illustrated by FIG. 6 and FIG. 10, the invention discloses a heater 209a;209b for inactivation of viruses in liquids and/or for general use in a bioreactor apparatus, comprising:

a) One or more segments 224 of a disposable heater conduit 215. The disposable heater conduit can e.g. be a flexible tubular structure with any cross section geometry, including a flexible bag 215a. Non-limiting examples of cross section geometries include circular, elliptical, rectangular, rhombic etc. The conduit may e.g. be made from plastic or an elastomer such as silicone rubber.

b) One or more metallic structures 222 inside said one or more segments. The metallic structures may e.g. comprise one or more lengths of metal pipe, metal mesh, metal braid or metal coil and it may suitably comprise a ferromagnetic metal, e.g. a ferromagnetic stainless steel. The metallic structure may be shaped to provide a large heat-transfer contact surface with fluids present in the heater conduit and to provide a low degree of hindrance to fluid flow through the conduit. The metallic structure can e.g. be tubular, such as a pipe, a tubular braid or a tubular mesh. Tubular meshes and braids provide particularly large contact surfaces. The metallic structure can have a length $l_{metal}$, in an axial direction of the heater conduit.

c) One or more induction coils 221 arranged to heat the one or more metallic structures by induction. The induction coil can be connected to a source 223 of high frequency alternating current (e.g. 5-400 kHz AC). The shape and dimensions of the coil, the frequency and the voltage can suitably be adjusted according to principles well known in the field of induction heating. A suitable degree of heating can then be achieved as discussed below. The one or more induction coils 221 may at least partially surround the one or more segments. They can completely surround the segments as shown in FIG. 6, but the coil(s) may also be e.g. U-shaped and only partially surround the segment(s), such that the segment can be inserted into the coil from the side. The coil can have a length $l_{coil}$ in an axial direction of the heater conduit, which may e.g. be equal to or shorter than $l_{metal}$. It can be advantageous if $l_{metal}$ is greater than $l_{coil}$, e.g. where $l_{metal}$ is at least 1.1 times greater than $l_{coil}$, such as at least 1.5 times greater, 1.1-5 times greater or 1.5-5 times greater. In these cases the coil will heat the metallic structure immediately inside the coil and heat will be rapidly conducted to the parts of the metallic structure outside the coil, where it can be efficiently transferred to the fluid due to the large area of the longer metallic structure. It is also possible to have other geometries of the induction heater. The coil(s) may e.g. comprise at least one flat coil segment 221a with leads 233 for a HF AC source, as illustrated in FIG. 10. Such a flat coil segment can be placed adjacent to an essentially flat sheet 222a of metal or metal mesh in the conduit segment. This sheet of metal or metal mesh can suitably be arranged in a plane 230 which is essentially parallel to a plane 231 of the at least one flat coil segment. The conduit segment can in this case conveniently be a flexible bag 215a, such as a pillow bag in a more or less flat configuration, which may e.g. be resting on a support plate 232 or clamped between two plates. As discussed above, the heater may be equipped with temperature sensors connected to a control unit, which may control the current source and allow feedback loop control of the temperature.

A method of heating a liquid can be to place a metal object, such as a hollow metal cylinder or a hollow cylinder made from a metal mesh, inside a plastic/silicone tube and heating the metal object using the principle of inductive heating. The inductive heating coil which provides the heating power remains outside of the tube and thus outside of the sterile barrier created by the tube. The metal object is in direct contact with the liquid inside of the sterile barrier created by the plastic/silicone tube. The electromagnetic field created by the inductive heating coil passes through the plastic/silicone tube and creates a heating effect in the metal object inside the tube. The heat generated in the metal then passes directly to the liquid or fluid by conduction. The metal inside the tube which contacts the liquid can take the shape of a multitude of geometries other than a hollow cylinder. The geometry is suitably selected to maximize the transfer of electromagnetic energy from the heating coil to the metal object inside the tube. Other possible geometries may be a bundle of metal rods, a bundle of hollow metal tubes, a spiral coil, objects with lobes shaped cross sections, etc. The length of this assembly is selected so as to produce sufficient heating of the liquid while it is resident in the tube as the liquid flows through the system.

The invention also discloses a bioreactor apparatus 1;101; 201;301 for cultivation of cells, which comprises a) a disposable bioreactor vessel 2 with one or more walls 3,4,5 defining an inner volume 6 and at least one port 10 in the wall(s), wherein the disposable bioreactor vessel is positioned in a rigid support structure 8;108; and b) the induction heater as discussed above, wherein the disposable heater conduit 215 is fluidically connected to the disposable bioreactor vessel 2 via a port 10. The segment of the disposable heater conduit may form part of a media addition line 220, so that the heating may be utilized for virus inactivation as discussed above. Alternatively, or additionally, the segment of the disposable heater conduit may form part of an exhaust gas line 250 from the bioreactor vessel 2. In this case the efficient induction heating may be used to prevent condensation in the exhaust gas line, i.e. to keep the temperature of the exhaust gases above the dew point. This can be done in an exhaust line leading to a condenser 251, e.g. with a condensate recycle line 252, and further to a gas filter 253 to prevent premature condensation in the line but it is also possible to use the induction heater as a filter heater to prevent any condensation in the gas filter. In the latter case, the gas filter may form at least part of the disposable heater conduit.

Example 1

Figure 8:
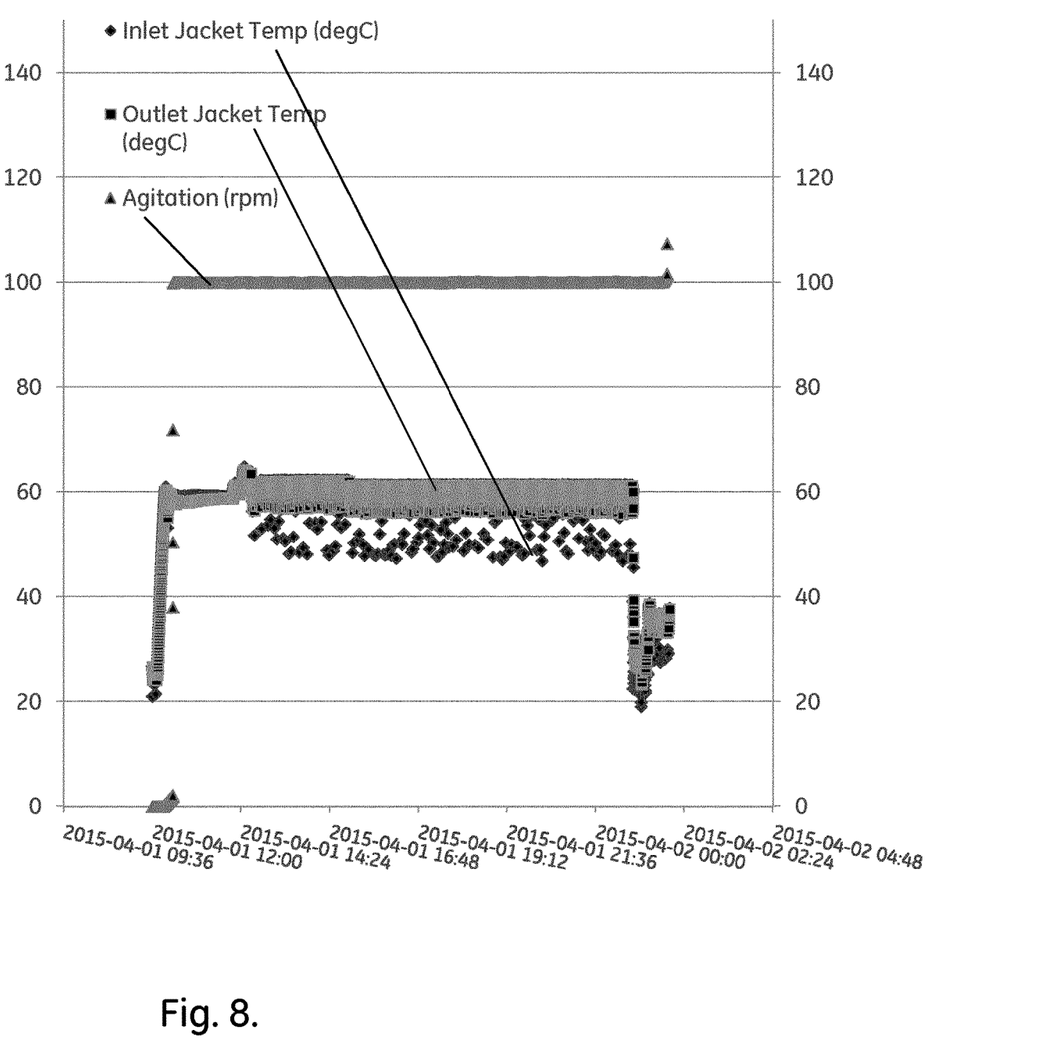
FIG. 8 shows temperature and rpm data for a 12 h heat treatment experiment according to the method of the invention.
Figure 9:
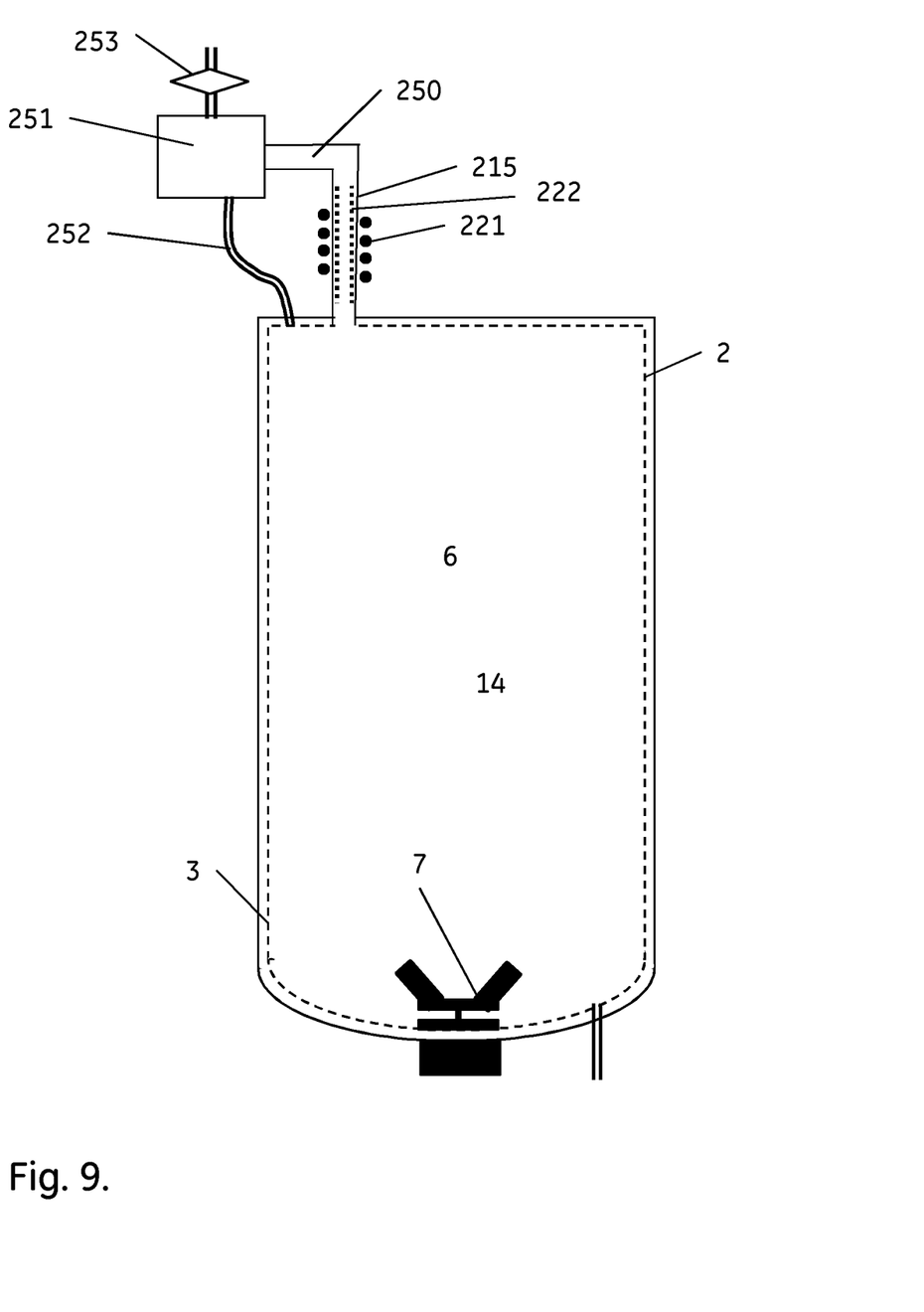
FIG. 9 shows a bioreactor apparatus according to the invention, side view.

A 500 L disposable bag with a magnetic impeller as shown in FIG. 5 was placed in a jacketed support vessel with temperature control liquid supplied by a TCU. The bag was filled with sterile filtered culture medium (LB SuperBroth+ glycerol) and was then subjected to a 12 h heating to 60° C. under 100 rpm agitation, as shown by the data in FIG. 8. The bag was then inoculated with bacteria, which were successfully cultivated for 30 h with no signs of bacteriophage infection.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A bioreactor apparatus for cultivation of cells comprising:
   a) a disposable bioreactor vessel with one or more walls defining an inner volume, at least one port in said one or more walls, wherein said disposable bioreactor vessel is positioned in a rigid support structure; and
   b) a heater, capable of heating an amount of culture medium to a target temperature in the range of 55-95° C., said amount of culture medium being confined in or conveyed to said inner volume,
   wherein said heater comprises a plastic or silicone disposable heater conduit fluidically-connected to said at least one port in said one or more walls of said disposable bioreactor vessel, and at least one heating element positioned to heat said disposable heater conduit,
   wherein the at least one heating element is duct-shaped and at least one segment of said disposable heater conduit is confined within the duct-shaped heating element wherein the at least one segment of said disposable heater conduit contains one or more metallic structures and wherein the at least one segment is at least partially surrounded by two or more induction coils, wherein the two or more induction coils are in series.

2. The bioreactor apparatus of claim 1, wherein said inner volume is at least 4 L.

3. The bioreactor apparatus of claim 1, wherein said disposable bioreactor vessel is a flexible bag.

4. The bioreactor apparatus of claim 1, wherein said disposable bioreactor vessel comprises at least one agitator in said inner volume.

5. The bioreactor apparatus of claim 1, wherein said heater is capable of heating an amount of culture medium corresponding to at least 20%, at least 50% or at least 60% of said inner volume to a target temperature in the range of 55-95° C.

6. The bioreactor apparatus of claim 1, wherein said rigid support structure has one or more walls defining an inner support volume and wherein said disposable bioreactor vessel has a shape conforming to, or essentially conforming to, a shape of said inner support volume.

7. The bioreactor apparatus of claim 1, wherein said heater is capable of maintaining said amount of culture medium within an interval of the target temperature+/−5° C.

8. The bioreactor apparatus of claim 1, wherein said one or more metallic structures comprise a ferromagnetic metal.

9. The bioreactor apparatus of claim 1, wherein said one or more metallic structures has an axial length $l_{metal}$ which is greater than an axial length $l_{coil}$ of said two or more induction coils.

10. The bioreactor apparatus of claim 9, wherein $l_{metal}$ is at least 1.1 times greater than $l_{coil}$.

11. The bioreactor apparatus of claim 10, further comprising a high-frequency alternating current power supply, electrically connected to said two or more induction coils.

* * * * *